United States Patent
Andersen et al.

(10) Patent No.: US 7,067,494 B2
(45) Date of Patent: Jun. 27, 2006

(54) ANTIMITOTIC ELEUTHESIDES

(75) Inventors: Raymond J. Andersen, Vancouver (CA); Michel Roberge, Vancouver (CA); Robert A. Britton, Cambridge (CA); E. Dilip De Silva, Vancouver (CA)

(73) Assignee: The University of British Columbia, Vancouver ( * ) Notice: Subject to any disclaimer, the term of this patent is extended or adjusted under 35 U.S.C. 154(b) by 244 days.

(21) Appl. No.: 10/481,688

(22) PCT Filed: Jun. 25, 2002

(86) PCT No.: PCT/CA02/00944

§ 371 (c)(1),
(2), (4) Date: Apr. 7, 2004

(87) PCT Pub. No.: WO03/000711

PCT Pub. Date: Jan. 3, 2003

(65) Prior Publication Data

US 2004/0266700 A1 Dec. 30, 2004

Related U.S. Application Data

(60) Provisional application No. 60/299,788, filed on Jun. 22, 2001.

(51) Int. Cl.
*A61K 31/7056* (2006.01)
*A61K 31/7048* (2006.01)
*C07H 17/08* (2006.01)

(52) U.S. Cl. ............... 514/32; 514/25; 536/17.4; 536/4.1

(58) Field of Classification Search ............... 536/17.4, 536/4.1; 514/25
See application file for complete search history.

(56) References Cited

U.S. PATENT DOCUMENTS

| | | | |
|---|---|---|---|
| 4,522,811 A | 6/1985 | Eppstein et al. | 514/2 |
| 4,960,790 A | 10/1990 | Stella et al. | 514/449 |
| 5,087,616 A | 2/1992 | Myers et al. | 514/21 |
| 5,420,105 A | 5/1995 | Gustavson et al. | 514/2 |
| 5,869,514 A | 2/1999 | Battistini et al. | 514/397 |
| 5,965,718 A | 10/1999 | Nicolaou et al. | 536/18.1 |
| 6,051,576 A | 4/2000 | Ashton et al. | 514/255.06 |
| 6,087,452 A | 7/2000 | Stewart et al. | 525/323 |
| 6,127,349 A | 10/2000 | Chasalow | 514/77 |
| 6,204,054 B1 | 3/2001 | Sutton et al. | 435/334 |
| 6,214,966 B1 | 4/2001 | Harris | 528/322 |
| 6,380,253 B1 | 4/2002 | Das | 514/560 |
| 2001/0034333 A1 | 10/2001 | Kosak | 514/44 |
| 2001/0041189 A1 | 11/2001 | Xu | 424/488 |

FOREIGN PATENT DOCUMENTS

| | | |
|---|---|---|
| WO | WO 89/11867 | 12/1989 |
| WO | WO 91/12023 | 8/1991 |
| WO | WO 96/14745 | 5/1996 |
| WO | WO 96/20218 | 7/1996 |
| WO | WO 96/36335 | 11/1996 |
| WO | WO 99/15157 | 4/1999 |
| WO | WO 99/21862 | 5/1999 |
| WO | WO 99/29704 | 6/1999 |
| WO | WO 99/59548 | 11/1999 |
| WO | WO 00/64471 | 11/2000 |
| WO | WO 01/15511 A2 | 3/2001 |
| WO | WO 01/28569 A1 | 4/2001 |
| WO | WO 01/38339 A1 | 5/2001 |

OTHER PUBLICATIONS

Bayer, FM., "The Shallow-Water Octocorallia of the West Indian Region", *The Hague*, 1961, Martinus Nighoff, 65, 75-77.

Britton, R., "Synthetic Transformation of Eleutherobin reveal New Features of its Microtubule-Stabilizing Pharmacophore", *Journal of the American Chemical Society*, 2001, 123(35), 8632-8633, XP002212128.

Brown, L. et al., Transdermal Delivery of Drugs, 1988, *Annual Review of Medicine*, 39, 221-229.

Cinel, B. et al., "Antimitotic Diterpenes from *Erythropodium Caribaeorum* Test Pharmacophore Models for Microtubule Stabilization", *Organic Letters*, 2000, 2(3), 257-260, XP-002159667.

Czerwinski, G. et al., "Cytotoxic Agents Directed to Peptide Hormone Receptors: Defining the Requirements for a Successful Drug", *Proc. Natl. Acad. Sci.*, 1998, 95, 11520-11525.

D'Ambrosio, M. et al., "Sarcodictyin A and Sarcodictyin B, Novel Diterpenoidic Alcohols Esterfied by (E)-N(1)-Methylurocanic Acid.Isolation from the Mediterranean Stolonifer *Sarcodictyon Roseum*", *Helv. Chim. Acta.*, 1987, 70, 2019-2027.

D'Ambrosio, M. et al., "Isolation from the Mediterranean Stoloniferan Coral *Sarcodictyon Roseum* of Sarcodictyin C,D,E, and F, Novel Diterpenoidic Alcohols Esterfied by (E)-or (Z)-N(1)-Methylurocanic Acid. Failure of the Carbon-Skeleton Type as a Classification Criterion", *Helvitca Chimica Acta.*, 1988, 71, 964-976.

(Continued)

*Primary Examiner*—Kamal A. Saeed
*Assistant Examiner*—Jason M. Nolan
(74) *Attorney, Agent, or Firm*—Woodcock Washburn LLP

(57) ABSTRACT

This invention provides analogs of eleutherobin and the eleuthesides modified at the C-11 position or comprising an epoxide functionality from C-11 to C-12. C-11 to C-12 is an ideal location for conjugating functional moieties to the eleutherobin pharmacophore without significant loss of antimitotic activity. Moieties that may be conjugated at C-11 include those intended to increase the solubility of the pharmacophore, to facilitate drug formulation, or to facilitate in vivo delivery or targeting.

17 Claims, No Drawings

OTHER PUBLICATIONS

Fenical, W. et al., "Defensive Properties of Secondary Metabolites from the Caribbean Gorgonian Coral *Erythopodium Caribaeorum*", *Marine Ecology Progress Series*, 1991, 75, 1-8.

Hooper, G.J. et al., "New Diterpenes from the South African Soft Coral *Eleutherobia Aurea*", *J. Nat. Prod.*, 1997, 60, 889-893.

Iwaski, S., "Studies on Macrocylic Lactone Antibiotics. IX 1) Novel Macrolides from the Fungus *Rhizopus Chinensis*: Precursors of Rhizoxin", *Chem Pharm Bull.*, 1986, 34, 1387-1390.

Ketzinel, S. et al., "Sarcodictyin A and Two Novel Diterpenoid Glycosides, Eleuthosides A and B, from the Soft Coral *Eleutherobia Aurea*", *J. Nat. Prod.*, 1996, 59, 873-875.

Kiyoto, S. et al., "A New Antitumor Complex, WF-1360, WF-1360A,B,C,D,E and F", *The Journal of Antibiotics*, 1986, (Tokyo), 39-762-772.

Lindel, T. et al., "Eleutherobin, a New Cytotoxin that Mimics Paclitaxel (Taxol) by Stabilizing Microtubules", *J. Am. Chem Soc.*, 1997, 119, 8744-8745.

Long, BH. Et al., "Eleutherobin, a Novel Cytotoxic Agent that Induces Tubulin Polymerization, is Similar to Paclitaxel (Taxol®) l", *Cancer Research*, 1998, 58, 1111-1115.

Nicolaou, K.C. et al., "Total Synthesis of Eleutherobin and Eleuthosides A and B", *J. Am. Chem. Soc.*, 1998, 120, 8674-8680.

Ojima, I. et al., "A Common Pharmacophore for Cytotoxic Natural Products that Stabilize Microtubules", *Proc. Natl. Acad. Sci.*, 1999, 96, 4256-4261.

Roberge, M. et al., "Cell-Based Screen for Antimitotic Agents and Identification of Analogues of Rhizoxin, Eleutherobin, and Paclitaxel in Natural Extracts", *Cancer Research*, 2000, 60(18), 5052-5058.

Stockwell, BR. et al., "High-Throughput Screening of Small Molecules in Miniaturized Mammalian Cell-Based Assays Involving Post-Translational Modifications", *Chemistry and Biology*, 1999, 6, 71-93.

Vincent, I. et al., "Mitotic Mechanisms in Alzheimer's Disease?", *The Journal of Cell Biology*, 1996, 132, 413-425.

ANTIMITOTIC ELEUTHESIDES

This application is a 371 of PCT/CA02/00944, filed Jun. 25, 2002. Acknowledgement is made of Applicant's claim for priority via U.S. Provisional application 60/299,788, filed on Jun. 22, 2001.

BACKGROUND OF THE INVENTION

Antimitotic compounds interfere with the dynamic assembly and disassembly of α- and β-tubulin into microtubules causing cells to arrest in mitosis. Prolonged arrest in mitosis eventually leads to cell death, often by apoptosis. Two chemical classes of antimitotic agents, the vinca alkaloids (vinblastine, vincristine, and vinorelbine) and the taxanes (paclitaxel and docetaxel), are clinically useful anticancer drugs. Most known antimitotic agents induce mitotic arrest by inhibiting the polymerization of tubulin into microtubules. This is the mechanism of the vinca alkaloids and rhizoxin.

Paclitaxel was the first chemical entity shown to cause mitotic arrest by stabilizing microtubules against depolymerization. Four additional chemotypes that have paclitaxel-like effects were later identified. These include the myxobacterium metabolites epothilones A and B, the marine sponge metabolites discodermolide, laulimalide, and isolaulimalide, and the soft coral terpenoid, eleutherobin (shown below). Ojima et al. (1999) Proc. Natl. Acad. Sci. USA 96:4256–4261, proposed a common pharmacophore for the microtubule stabilizing compounds that effectively accommodates nonataxel, paclitaxel, discodermolide, eleutherobin, and the epothilones. This model predicts that three regions of eleutherobin (boxes A, B, and C below) are important for binding to tubulin (Me=methyl; Ac=acetyl).

Eleutherobin Pharmacophore

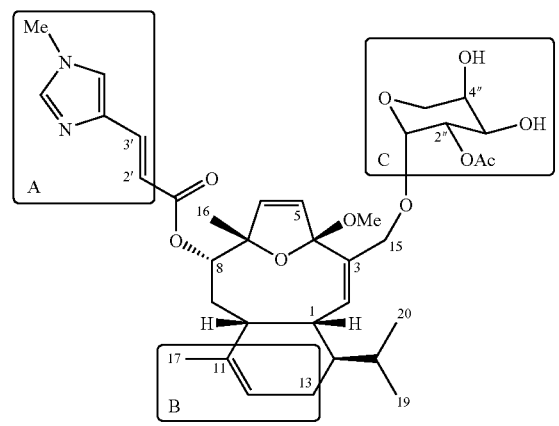

The majority of known antimitotic natural products were initially isolated because they exhibited potent in vitro cytotoxicity. Only subsequent detailed mechanism of action studies revealed that they arrested cells in mitosis and interfered with tubulin assembly and disassembly dynamics. For example, rhizoxin is a 16-membered ring macrolide first isolated in 1984 and determined to be very cytotoxic. Only later was rhizoxin shown to cause the accumulation of cells in mitosis. Sarcodictyins A-D were the first members of a cytotoxic terpenoid class of compounds to be identified (see: D'Ambrosio, M., et al. (1987) Helv. Chim. Acta. 70:2019–2027; and, (1988) Helv. Chim. Acta. 71:964–976), their paclitaxel-like properties being recognized only later.

Eleutherobin, a diterpene glycoside, was originally isolated from the soft coral Eleutherobia sp. (possibly E. albiflora) collected in Western Australia (see: Lindel, T. et al. (1997) J. Am. Chem. Soc. 119:8744–8745; and, international patent application published May 23, 1996 under WO 96/14745). Subsequently, eleuthesides A and B were isolated from a different species of Eleutherobia (E. aurea). The eleuthesides share the pharmacophore shown above but differ from eleutherobin by the presence of a hydroxyl substituent at the C-4 position of eleutherobin (rather than a methoxyl substituent) and by the presence of an acetyl group at the 3" or the 4" position of the arabinose moiety shown above, in addition to an acetyl at the 2" position (Ketzinel, S., et al. (1996) J. Nat. Prod. 59:873–875). Later, a total synthesis of eleutherobin and eleuthesides A and B was reported (Nicolaou, K. C., et al. (1998) J. Am. Chem. Soc. 120:8674–8680). As reported in the latter reference, the eleuthesides may be made by converting C-4 ketal precursors to C-4 hydroxyl forms. Eleutherobin and the eleuthesides are hydrophobic compounds.

International patent application published May 31, 2001 under WO 01/38339 disclosed use of a cell-based antimitotic assay which demonstrated potent antimitotic activity in extracts of various marine organisms. Microscopic examination of cells arrested in mitosis by some extracts showed tubulin bundling, similar to the effects of paclitaxel. Bioassay guided fractionation of these extracts led to the isolation of eleutherobin and other antimitotic diterpenes, including desmethyleleutherobin, desacetyleleutherobin, isoeleutherobin A, Z-eleutherobin, caribaeoside, and caribaeolin.

WO 01/38339 disclosed that certain alterations outside the Ojima, et al. [supra] pharmacophore binding regions resulted in changes in antimitotic potency. It was also shown that alterations at C-11 to C-13 of eleutherobin (region B of the pharmacophore) could significantly decrease potency, as shown by the measured antimitotic activities for caribaeoside and caribaeolin. Thus the prior art indicates that modifications to region B of the pharmacophore for eleutherobin or the eleuthesides should not be made if one wishes to retain antimitotic activity.

SUMMARY OF THE INVENTION

This invention is based on the discovery that modifications to region B of the eleutherobin pharmacophore need not be detrimental to antimitotic activity. As a result of this invention, region B of the pharmacophore becomes the location of choice for modification of eleutherobin and the eleuthesides or analogs thereof, where such modification is to affect the characteristics of the antimitotic compound for purposes of pharmaceutical formulation or to improve delivery of the antimitotic compound to a target in a patient.

This invention provides novel compounds suitable for use as antimitotic agents and as intermediates for the production of antimitotic agents. The novel compounds of this invention are based on modification in region B of the pharmacophore which permit retention of antimitotic activity. Antimitotic compounds of this invention or compounds made from compounds of this invention as intermediates can provide improved tolerance in patients at therapeutically effective doses (improved therapeutic index) through better delivery of an effective dose of the compound to tissues or cells within a patient by the compound acting as a prodrug, or by the compound being joined to another therapeutic agent.

This invention provides an antimitotic compound and pharmaceutical preparations thereof, wherein the compound is a compound of formula I or II:

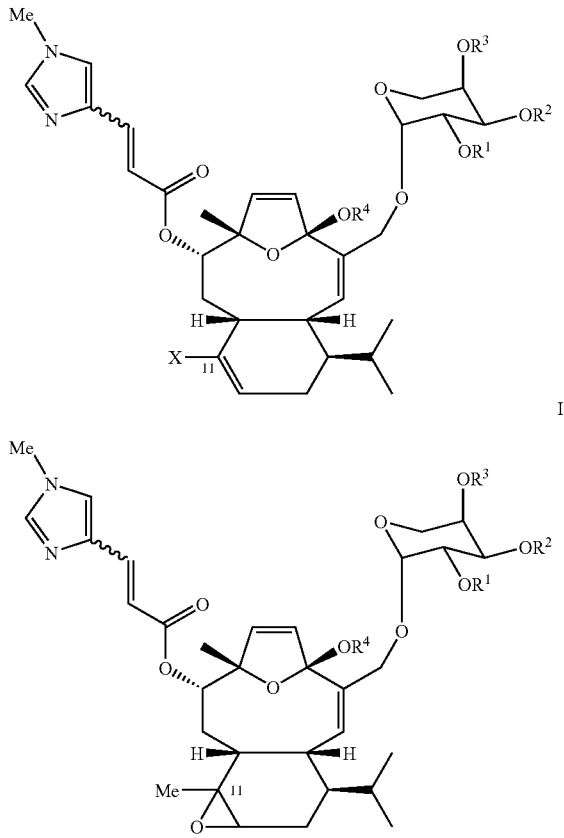

In compounds of this invention, Me is methyl; $R^1$, $R^2$ and $R^3$ are independently selected from the group consisting of H and a $C_1$–$C_6$ acyl; and, $R^4$ is selected from the group consisting of H, Me and a substituted or unsubstituted straight-chain, branched, or cyclic $C_1$–$C_{10}$ alkyl. Preferably, an acyl in $R^1$–$R^4$ is acetyl and an alkyl in $R^1$–$R^4$ is a $C_2$–$C_5$ straight-chain or branched moiety. Any or all of $R^1$–$R^4$ may be selected independent of whether the compound is of formula I or II and the identify of X in formula I.

Preferred embodiments of this invention include those in which: $R^1$ and $R^2$ are H and $R^3$ is Ac; $R^4$ is H, ethyl, propyl, butyl or pentyl; one of $R^1$ and $R^2$ is H and the other Ac; and, $R^3$ is H. In other preferred embodiments: $R^4$ is Me; $R^1$ and $R^3$ are H; and, $R^2$ is Ac.

In compounds of formula I of this invention, X is a moiety other than methyl, bound through one carbon atom directly to the C-11 position. Thus, X cannot consist of methyl or hydrogen, or comprise a heteroatom joined directly to C-11. X may be any functional moiety selected to provide a physical characteristic (such as solubility), to provide a chemical characteristic (such as reactivity with another moiety to be joined to a compound of formula I), or to provide a desired performance in vivo (such as enhanced circulation longevity or targeting to a particular cell or tissue).

In compounds of formula I, X may be selected from the group consisting of: —$CH_2OR$; —COR; —COY; —C(OR)R; —$CRCR_2$; and, —$CH_2W$. R may be selected from the group consisting of: H; a linear, branched, or cyclic, saturated or unsaturated alkyl group containing one to ten carbons that may be substituted with Z; an aromatic group such as phenyl, napthyl, anthracyl, phenanthryl, furan, pyrrole, thiophene, benzofuran, benzothiophene, quinolinc, isoquinoline, imidazole, thiazole, oxazole, or pyridine and the aromatic group may be substituted with Z; and, arylalkyl (ArR*) where the alkyl group (R*) may be linear, branched, or cyclic, and saturated or unsaturated containing one to ten carbons that may be substituted with Z and the aryl group (Ar) may be phenyl, napthyl, anthracyl, phenanthryl, furan, pyrrole, thiophene, benzofuran, benzothiophene, quinoline, isoquinoline, imidazole, thiazole, oxazole, or pyridine that may be substituted with Z. Z may be selected from the group consisting of: —OH, —OR, —$O_2CR$, —SH, —SR, —SOCR, —$NH_2$, —NHR, —$NHR_2$, —NHCOR, —NRCOR, —I, —Br, —Cl, —F, —CN, —$CO_2H$, —$CO_2R$, —CHO, —COR, —$CONH_2$, —CONHR, —$CONR_2$, —COSH, —COSR, —$NO_2$, —$SO_3H$, —SOR, and —$SO_2R$ (with R being as defined above). Y may be selected from the group consisting of: —OH, —$NH_2$, —NHR, —$NR_2$, —SH, —SR and —OR (with R being as defined above). W may be selected from the group consisting of: R, F, Cl, Br, I, —$OSO_3R$, —$SO_3R$, —$OPO_3R_2$, —$PO_3R_2$, —SR, —SOR, —$SO_2R$, —$NR_2$, —NOR, and —$NR_3^+$, with R being as defined above. In R*, and when R comprises an alkyl group, —$CH_2$— may be replaced by —$O_2S$ or NR, and CH may be replaced by N. Each R may be the same or different.

Preferred compounds of this invention are compounds of formula I in which X is as defined above with R being H, or a linear, branched or cyclic, saturated or unsaturated alkyl group and Y being: —OH, —$NH_2$, —NHR, —$NR_2$ or —OR; or, compounds of formula II. In some preferred compounds of formula I, R is H or an alkyl group, which is preferably a $C_1$–$C_6$ branched or straight chain moiety.

A compound of this invention includes salts (preferably pharmaceutically acceptable salts) and also includes isomers, including those of the Z and E configurations, those of the α and β configurations at the glycosidic bond and the α and β configurations of the epoxide at C-11 to C-12 in formula II.

This invention also provides the use of a compound or a pharmaceutical preparation of this invention as an antimitotic agent and for the preparation of antimitotic agents including medicaments. This invention also provides a method for causing mitotic arrest in one or more cells present in a cell population, comprising treating the cell population with a sufficient amount of a compound or pharmaceutical preparation of this invention to arrest mitosis in one or more cells in the cell population. The cell population may be a population of cancerous cells, including a tumor. This method may be performed in vitro or may be performed in vivo through administration to a human or animal patient with a cancer.

DETAILED DESCRIPTION

The structure of compounds of this invention is of a broad scope in as much as substituent X in compounds of formula I may be any moiety selected to confer a desired characteristic different from that provided when a methyl group is joined at C-11 (as is the case for the naturally occurring compounds). Moiety X will be joined to the pharmacophore through a carbon atom bound directly to C-11. This means that C-17 found in the naturally occurring compounds is retained, but is not methyl. Moiety X may be a polar group selected to increase the solubility of the compound. Such a polar group includes an ionizable group, which would facilitate the formation of salts, such as pharmaceutically acceptable acid-addition salts. Increasing the solubility of antimitotic compounds of this invention facilitates formulation of the compounds thereby permitting one to avoid difficulties associated with formulation of hydrophobic drugs. One example of such a substituent joined at C-11 as described in the Examples below is —COH or —COOH. The latter substituent is ideally suited for forming salts.

Moiety X of compounds of formula I of this invention may be selected to increase the reactivity of region B of the pharmacophore, thereby permitting compounds of this invention to function as intermediates in the preparation of compounds in which other chemical moieties are joined to the pharmacophore at region B. Examples of moiety X as described in the Examples below, which increase the reactivity of region B for joining to other moieties while retaining stability include: —$CNH_2$ and —COOH. The latter substituents are ideally suited for joining to amine or carboxylic acid-containing moieties by means of a peptide linkage. Likewise, compounds of formula II of this invention represent stable antimitotic compounds having a modification in region B that facilitates conjugation to another moiety (see Example 9 below).

Moiety X of compounds of formula I may be a substituent which comprises a linker which in turn may be used for conjunction to another functional group. Such a linker may be any linker known in the art for joining biologically active compounds or for joining a biologically active compound to a carrier. Such linkers may be cleavable upon the action of an agent present at or near a target site (e.g. reduced pH) or which is administered in conjunction with the compound of this invention. An example of such linkers are those described by Czerwinski, et al. (1998) Proc. Natl. Acad. Sci. 95:11520–11525, in WO 89/11867 and WO 91/12023, or the metal chelating linkages described in WO 00/64471, WO 01/28569, and U.S. Pat. No. 6,087,452.

Compounds of this invention include compounds intended for use as intermediates (for example to be joined to another chemical moiety) and include the resulting products in which moiety X is joined to C-11 as in compounds of formula I. Thus, moiety X of compounds of formula I may be any functional group or moiety selected to provide a desired performance in vivo. Without limitation, moiety X may comprise a peptide (including polypeptides and proteins), a lipid, a polysaccharide, a pharmaceutically compatible polymer or another drug. Thus, compounds of formula I of this invention include compounds that are conjugated to a lipid in a lipid-based delivery vehicle such as a liposome, to a peptide that facilitates transfer across a cell membrane, to an antibody having specificity for a target cell and to a peptide ligand capable of binding to a cell surface receptor or the like. In other embodiments, moiety X comprises a polymer suitable for incorporation within a pharmaceutical preparation or which enhances delivery of an active compound within the body.

Moiety X is joined to a compound of formula I at the C-11 position through at least one carbon atom bound directly to C-11. Such direct binding of the carbon atom to C-11 is by a covalent bond. However, the remainder of moiety X may comprise components which are joined together or to the carbon atom that is bound to C-11, through any form of conjugation. By the terms "conjugation" and "conjugated" it is meant that components are joined by any of covalent bonds, coordinate covalent bonds, ionic bonds and hydrogen bonds.

The physical, chemical, or biological characteristics of the pharmacophore can be altered in many ways that would be apparent to persons skilled in the art. Different functional groups will alter the solubility of the pharmacophore through the addition of groups that for example alter polarity and/or the ability to form hydrogen bonds. Similarly a functional group may alter the stability of the pharmacophore by changing the serum half-life or by controlling the release of the pharmacophore from a micelle at the target site or converting a prodrug to the active form at the target site. Further a functional group may alter the biocompatibility of a pharmacophore for example by minimizing the side effects of the drug to the patient. A functional group may further enhance delivery and targeting of the pharmacophore through the addition of a functional group capable of binding the target cells or tissues or facilitating the transport into the target cells. The functional group may also enhance the anti-tumor activity of the pharmacophore if for example the pharmacophore is conjugated to another anti-proliferative drug. A person skilled in the art will appreciate what type of functional groups might be added to achieve the desired result in administering the pharmacophore to the patient and thereby improving the overall therapeutic index.

A functional group conjugated to the pharmacophore may be a biological targeting molecule that binds to a specific biological substance or site. The biological substance or site is the intended target of the delivery and targeting molecule that binds to it, enabling the delivery of the pharmacophore to the tissue or cells of interest.

A ligand may function as a biological targeting molecule by selectively binding or having a specific affinity for another substance. A ligand is recognized and bound by a specific binding body or binding partner, or receptor. Examples of ligands suitable for targeting are antigens, haptens, biotin, biotin derivatives, lectins, galactosamine and fucosylamine moieties, receptors, substrates, coenzymes and cofactors among others. A ligand may include cancer and tumor antigens such as alpha-fetoproteins, prostate specific antigen (PSA) and CEA, cancer markers and oncoproteins, among others. Other substances that can function as ligands for delivery and targeting are certain steroids, prostaglandins, carbohydrates, lipids, certain proteins or protein fragments (i.e. hormones, toxins), and synthetic or natural polypeptides with cell affinity. Ligands also include various substances with selective affinity for ligators that are produced through recombinant DNA, genetic and molecular engineering.

Another type of targeting molecule is an antibody, which term is used herein to include all classes of antibodies, monoclonal antibodies, chimeric antibodies, Fab fractions, fragments and derivatives thereof. Other targeting molecules include enzymes, especially cell surface enzymes such as neuraminidases, plasma proteins, avidins, streptavidins, chalones, cavitands, thyroglobulin, intrinsic factor, globulins, chelators, surfactants, organometaffic substances, staphylococcal protein A, protein G, cytochromes, lectins, certain resins, and organic polymers. Targeting molecules may include peptides, including proteins, protein fragments or polypeptides which may be produced synthetically or through recombinant techniques known in the art. Examples of peptides include membrane transfer proteins which could facilitate the transfer of the pharmacophore to a target cell interior or for nuclear translocation (see: WO 01/15511).

Other examples of moieties which may facilitate transfer into a target cell are described in U.S. Pat. No. 6,204,054, which includes transcytosis vehicles and enhancers capable of transporting physiologically-active agents across epithelia, endothelia and mesothelia containing the GP60 receptor. The GP60 receptor has been implicated in receptor-mediated transcytosis of albumin across cell barriers. U.S. Pat. No. 6,204,054 exploits GP60 receptor-mediated trauscytosis for the transport of physiologically-active agents which do not naturally pass through epithelia, endothelia and mesothelia via the GP60 system. The pharmacophore can be coupled to albumin, albumin fragments, anti-GP60 polyclonal and monoclonal antibodies, anti-GP60 polyclonal and monoclonal antibody fragments, and GP60 peptide fragments to facilitate transport into the cell.

Conjugation to a functional group may also improve other properties of the pharmacophore. Such functional groups may be termed drug carriers and can improve the solubility, stability, or biocompatibility of the drug being carried. For example the solubility of the pharmacophore may be improved by conjugating the pharmacophore to a peptide polymer. By way of example U.S. Pat. Publication No. 2001041189 describes the use of polypeptides (containing glutamic acid and aspartic acid, or glutamic acid/alanine, or glutamic acid/asparagine, or glutamic acid/glutamine, or glutamic acid/glycine) conjugated to hydrophobic drugs such as paclitaxel to act as carriers to improve the solubility of the drugs and/or their therapeutic efficacy in vivo. Similarly, U.S. Pat. No. 5,087,616 describes the use of a biodegradable polymeric carrier (a homopolymer of polyglutamic acid) to which one or more cytotoxic molecules, such as daunomycin is conjugated Also by way of example, U.S. Pat. No. 4,960,790 describes paclitaxel covalently conjugated to an amino acid (glutamic acid) to improve drug solubility. Another example is described in U.S. Pat. No. 5,420,105, where polypeptide carriers capable of binding one drug or multiple drugs can further be attached to a targeting or delivery protein, such as an antibody or ligand capable of binding to a desired target site in vivo.

Another example of a drug carrier is described in U.S. Pat. Publication No. 2001034333, where cyclodextrin polymers are used for carrying drugs and other active agents for therapeutic, medical or other uses. The 2001034333 specification also discloses methods for preparing compositions of cyclodextrin polymer carriers that are further coupled to delivery and targeting molecules to deliver drugs, like paclitaxel and doxorubicin, to their site of action.

By way of a further example, U.S. Pat. No. 6,127,349 describes the use of phospholipids to improve the solubility of the therapeutic agents(steroids, peptides, antibiotics and other biologically active agents and pharmaceutical formulations) and to improve their bio-availability. Similarly, fatty acids could be conjugated to the pharmacophore in order to stabilize the activity of the anti-angiogenic substances. By way of example U.S. Pat. No. 6,380,253 describes the conjugation of anti-angiogenic substances (proteins—angiostatin and endostatin etc.) to cis-unsaturated fatty acids or polyunsaturated fatty acids to potentiate and stabilize the activity of the anti-angiogenic substances.

Other suitable drug carriers include biologically compatible polymers such as polyethylene glycol (PEG) and related polymer derivatives. Drug-PEG conjugates have been described as improving the circulation time (prolong serum half-life) before hydrolytic breakdown of the conjugate and subsequent release of the bound molecule thus increasing the drugs efficacy. For example, U.S. Pat. No. 6,214,966 describes the use of PEG and related polymer derivatives to conjugate to drugs such as proteins, enzymes and small molecules to improve the solubility and to facilitate controlled release of the drug. Alternatively, EP 1082105 (WO 99/59548) describes the use of biodegradable polyester polymers as a drug delivery system to facilitate controlled release of the conjugated drug.

As another alternative the pharmacophore may be conjugated to another pharmaceutically active compound to enhance the therapeutic effect on the target cell or tissue by delivering a second compound with a similar anti-mitotic effect or a different activity altogether. For example, U.S. Pat. No. 6,051,576 describes the use of co-drug formulations by conjugating two or more agents via a labile linkage to improve the pharmaceutical and pharmacological properties of pharmacologically active compounds.

Compounds of this invention may be made from eleutherobin and eleuthoside compounds isolated from natural sources, such as is described in WO 01/38339. Alternately, compounds of this invention may be prepared by total synthesis by adapting the methods of Nicolaou, K. C., et al. [supra] and those disclosed in WO 01/38339 using conventional starting materials, or from intermediates prepared by reduction and glycosylation of sarcodictyin A (see: WO 96/14745). Intermediates used in the preparation of compounds of this invention may include isoeleutherobin A, desmethyleleutherobin or eleutherobin, with appropriate substitutions at $R^{1-3}$ done using conventional procedures.

At one time, the only known natural source of eleutherobin was a species of soft coral from Western Australia (see: Lindel, T. et al. [supra]. WO 01/38339 disclosed an abundant new source of antimitotic terpenoids from a taxonomic order of coral and coral-like organisms much different from the order Alcyoniidae which comprises the soft coral described by Lindel, T. et al. Using assays specifically adapted to detect antimitotic compounds, it was determined that organisms of the order Gorgonacea produce such antimitotic compounds. Such organisms include species of the genus *Erythropodium*; species of the genus *Rumphella* (family Gorgoniidae); *Mopsea whiteleggei* and *Muricellisis* Sp. a (family Isididae); *Subergorgia* Sp. 1 cf *Mollis* and *Subergorgia Mollis* (geog. variant) (family Subergorgiidae); and, *Junceella* Sp. d. *Verrucella* Sp. b and *Ctenosella regia* (family Ellisellidae).

A preferred natural source of intermediate compounds for use in preparing compounds of this invention are the gorgonian corals, and in particular, *Erythropodium caribaeorun*. Gorgonian corals are found in all tropical and subtropical regions, particularly the Caribbean. These corals are found in abundance, and have been grown in aquarium environments and may be readily identified (for example, see: Bayer, F. M.; "The Shallow-Water Octocorallia of the West Indian Region" (1961) Martinus Nighoff; The Hague, at page 65 and 75–77 for *Erythropodium*). *E. caribaeorum* may be collected in abundance from southern Florida to the Virgin Islands.

Methods suitable for assaying antimitotic activity of compounds of this invention or compounds used as precursors, may be based on the use of antibodies specific for mitotic cells, such as those described in the international patent application published Apr. 1, 1999 under WO 99/15157 or the assay described in WO 01/38339. Such an assay will typically employ cells which regularly divide in culture (e.g. cancer cells). A known antimitotic compound such as nocodazole may be used as a control. In the assay, determination of the cells which proceed to mitosis is carried out using any of the known immunological methods by employing antibodies which have specificity for mitotic cells. Monoclonal antibodies demonstrating such specificity are known and include MPM-2 which was raised against mitotic HeLa cells and recognizes phospho-epitopes that are highly conserved in mitotic proteins of all eukaryotic species. Other examples are the monoclonal antibodies recognizing phospho-epitopes in the paired helical filament proteins (PHF) found in brain tissue of patients suffering from Alzheiner's disease as described in: PCT International Application published Jul. 4, 1996 under No. WO 96/20218; and, Vincent et al. (1996) "The Journal of Cell Biology", 132:413–425. TG-3 antibody described in the latter two references may be obtained from Albert Einstein College of Medicine of Yeshiva University, Bronx, N.Y. This antibody is highly specific for mitotic cells and functions in ELISA.

Immunological methods useful for determination of mitotic cells in an assay include any method for determining antibody-antigen binding, including: immunocytochemistry (e.g. immunofluorescence), flow cytometry, immunoblotting, and ELISA, including those described in Vincent, I. et al. [supra]. High throughput testing of samples may be readily achieved by use of the ELISA or the ELICA assays described in WO 01/38339.

Pharmaceutical preparations containing compounds of this invention may be prepared as for similar preparations containing eleutherobin, paclitaxel, etc. In the case of compounds of this invention capable of salt formulation, pharmaceutically acceptable salts may be used to advantage to permit administration of the compound in an aqueous solvent. Modes of administration to an animal or human patient include intravenous and intraperitoneal, to achieve a circulating concentration of the drug as predicted from its activity using standard methodology.

A human or other animal patient suffering from proliferative diseases, and other similar conditions may be treated by administering to the patient an effective amount of one or more of the compounds of this invention or a pharmaceutically acceptable derivative or salt thereof, in a pharmaceutically acceptable carrier or diluent. The active materials can be administered by any appropriate route, for example, orally, parenterally, intravenously, intradermally, or subcutaneously.

The term pharmaceutically acceptable salts or derivatives refers to salts or complexes that retain the antimitotic activity of the compound and exhibit minimal undesired toxicological effects. Nonlmiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid; (b) base addition salts formed with polyvalent metal cations such as zinc, calcium, bismuth, barium, magnesium, aluminum, copper, cobalt, nickel, cadmium, sodium, potassium, and the like, or with an organic cation formed from N,N-benzylethylene-diamine, D-glucosamine, ammonium, tetraethylammonium, or ethylenediamine; or (c) combinations of (a) and (b); e.g., a zinc tannate salt or the like.

A compound of this invention or salt thereof, may be included in a pharmaceutically acceptable carrier or diluent, ideally in an amount sufficient to deliver to a patient a therapeutically effective amount without causing serious toxic effects in the patient treated. The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgement of the person administering or supervising the administration of the compositions.

Solutions or suspensions used for parenteral, intradermal, subcutaneous, or topical application may include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of toxicity such as sodium chloride or dextrose.

Suitable pharmaceutically acceptable carriers for parenteral application, such as intravenous, subcutaneous, or intramuscular injection, include sterile water, physiological saline, bacteriostatic saline (saline containing 0.9 mg/ml benzyl alcohol) and phosphate-buffered saline. If administered intravenously, preferred carriers are physiological saline or phosphate buffered saline (PBS). Methods for preparing transdermal patches are known to those skilled in the art. For example, see Brown L., and Langer R., *Transdermal Delivery of Drugs* (1988), Annual Review of Medicine, 39:221–229.

Compounds of this invention may be prepared with carriers that will protect the compound against rapid elimination from the body, such as through controlled release formulations, including implants and microencapsulated delivery systems. Biodegradable, biocompatible polymers can be used, such as ethylene vinyl acetate, polyanhydrides, polyglycolic acid, collagen, polyorthoesters, and polylactic acid.

Liposomal suspensions are also suitable carriers for compounds of this invention. The compounds may be conjugated to a lipid by known methods for incorporation into a liposomal envelope or the compounds may be encapsulated into the liposome. Liposomes may be prepared according to methods known to those skilled in the art, such as is described in U.S. Pat. No. 4,522,811. For example, liposome formulations may be prepared by dissolving appropriate lipid(s) (such as stearoyl phosphatidyl ethanolamine stearoyl phosphatidyl choline, arachadoyl phosphatidy choline, and cholesterol) in an inorganic solvent that is then evaporated, leaving behind a thin film of dried lipid on the surface of the container. An aqueous solution of the active compound or its monophosphate, and/or triphosphate derivatives are then introduced into the container. The container is then swirled by hand to free the lipid aggregates, thereby forming the liposomal suspension.

Oral compositions may include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition. Methods for encapsulating compositions (such as in a coating of hard gelatin) for oral administration are well known in the art (Baker, Richard, *Controlled Release of Biological Active Agents*, John Wiley and Sons, 1986).

Tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, or corn starch; a lubricant such as magnesium stearate; a glidant such as colloidal silicon dioxide; a sweetening agent such as sucrose or saccharin; or a flavouring agent such as peppermint, methyl salicylate, or orange flavouring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents. Alternatively, compounds of this invention could be administered as a component of an elixir, suspension, syrup, wafer, chewing gum or the like. A syrup may contain, in addition to the active compounds, sucrose as a sweetening agent and certain preservatives, dyes and colourings and flavours.

EXAMPLES

Synthesis from Eleutherobin

Example 1

The first objective was to trap the C-4 ketone in eleutherobin as a cyclic ketal in order to liberate the C-4/C-7 ether oxygen as a C-7 alcohol and to change the oxygen atom's spatial relationship with the C-14 isopropyl group. In order to test the reactivity of the C-4 hemiketal, desmethyleleutherobin 2 was treated with various neat aliphatic alcohols (ROH: ethanol, n-propanol, n-butanol or isopropanol) and excess pyridinium p-toluenesulfonate (PPTS) at room temperature (rt), which gave quantitative conversion to the corresponding C-4 ketal analogs (Table 1). Attempts to make the C-4 cyclic ketals of 2 with ethylene glycol or 2,2-dimethyl-1,3-propanediol under a variety of conditions using PPTS as a catalyst only gave the ketals 3 and 4 which were comparable in antimitotic activity ($IC_{50}$=20 nM and 80 nM respectively) to eleutherobin ($IC_{50}$ 20 nM). The x-ray structure of eleutherobin shows significant distortion of the C-1/C-2/C-3 (132š) and C-2/C-3/C-4 (127š) bond angles. This angle strain may act like a clamp to keep the dihydrofuran ring from opening during the transketalization reactions.

TABLE 1

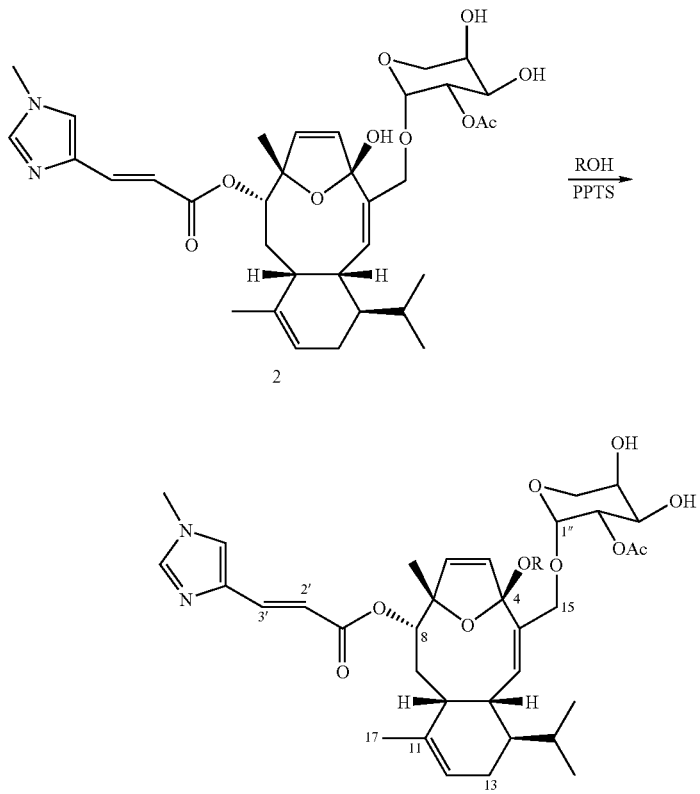

1 R = Me

TABLE 1-continued

3 R = 

4 R = 

Example 2

Oxidation reactions involving the Δ11,12 olefin of eleutherobin 1 were performed (Table 2). Reaction of 1 with m-chloroperbenzoic acid (MCPBA) in $CH_2Cl_2$ at rt for 8 h gave a mixture of only two epoxides, 5 and 6. The 1H NMR data obtained for both 5 and 6 showed the absence of a resonance that could be assigned to H-12 and in both spectra the Me-17 resonance had undergone a significant upfield shift. The observation of a 1D NOESY correlation between the Me-17 resonance at δ and the H-2 resonance at δ showed that the major epoxide was the β isomer 5. Treatment of 1 with $SeO_2$ (0.5 equiv.) in refluxing ethanol (EtOH) gave a single product 7 in modest yield. The α and β epoxides 5 and 6 (which are compounds of formula II of this invention) and the 17-hydroxyeleutheside 7 (which is a compound of formula I of this invention) all had antimitotic potencies comparable to eleutherobin. The $IC_{50}$ values on the above-described cell based mitotic assay were 300 nM, 30 nM and 20 nM for compounds 5, 6, and 7 respectively. Compounds 5 and 6 are particularly suited for use as intermediates given the stable but reactive nature of the epoxide functionality. Compound 7 is particularly suitable as an intermediate for the same reasons and is less hydrophobic than eleutherobin, thereby allowing for the formulation of a more soluble pharmaceutical preparation of the compound, as compared to eleutherobin.

TABLE 2

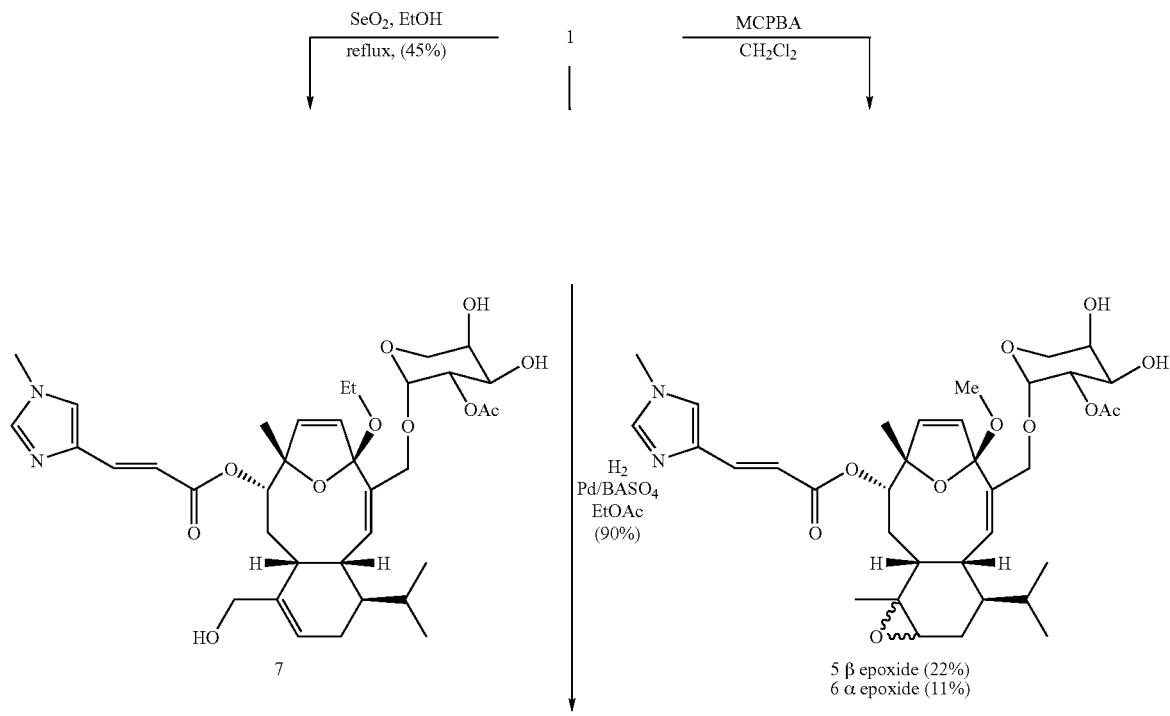

TABLE 2-continued

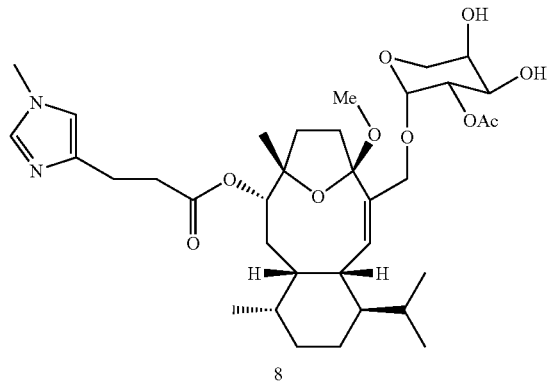

8

Example 3

Reduction of the olefins in 1 was examined. A solution of eleutherobin in ethyl acetate (EtOAc) containing catalytic palladium (Pd) on BaSO4 was stirred at rt for 1 h under 1 atm of $H_2$ resulting in the formation of hexahydroeleutherobin 8 (Table 2). The 1H NMR data obtained for 8, which contained only a single olefinic proton resonance at δ 5.78 (d, J=9.3 Hz) assigned to H-2, clearly indicated that the Δ5,6, Δ11,12, and Δ2',3' double bonds had been reduced. A 1D NOESY enhancement observed between the Me-17 resonance at δ 0.76 (d, J=7.0 Hz) and the H-2 resonance at δ 5.78 demonstrated that hydrogen had added to the more accessible β face of the Δ11,12 olefin. Hexahydroeleutherobin 8 ($IC_{50}>10^4$ nM was found to be more than five thousand fold less active than eleutherobin, indicating that the presence of one or more of the reduced double bonds affects tubulin binding. Previous evaluation of a synthetic sarcodictyin library had suggested that reduction of the Δ5,6 olefin had minimal effect on the potency of tubulin polymerization. (Nicolaou, K. C. et al. (1998) J. Am. Chem. Soc. 120:10814–26). Therefore, 5,6, 11,12-tetrahydroeleutherobin (9) and 2',3'-dihydroeleutherobin (10) were selected as targets to further probe the biological effects of olefin reduction.

Example 4

The synthesis of 9 started from eleutherobin, through first forming the 3",4"-acetonide 11, which was subsequently deacetylated to the 2" alcohol and converted directly to the 2" TBS ether 12. Hydrogenation of 12, using catalytic Pd on BaSO4, gave the 5,6,11β,12,2',3'-hexahydro derivative vide supra (Table 3). Hydrolysis of the crude hydrogenation product cleanly removed the C-8 ester side chain, which was replaced with a urocanic ester residue 4c to afford 14. Deprotection of the tribromosalicylanilide (TBS) protecting group, followed by acetylation of the formed 2" alcohol provided 15, which was subsequently deprotected under mildly acidic conditions to give 5,6,11β,12-tetrahydro eleutherobin (9). Similarly, 2'3'-dihdro-eleutherobin (10) was prepared from the 2" TBS ether 12, by hydrolysis of the urocanic ester residue (NaOH, MeOH) to provide a secondary alcohol at C-8, which was directly coupled with 2,3-dihydro-urocanic acid (17) using 1,3-dichlorohexylcarbodiimide (DCC) and 4-dimethylaminopyridine (DMAP) in warm (50° C.) dimethyl formanide (DMF) to afford 15. A deprotection/acetylation sequence similar to that employed in the synthesis of the tetrahydro derivative 9, provided 10 in good yield. Compound 9 exhibited antimitotic activity ($IC_5$ 200 nM) comparable to eleutherobin while compound 10 demonstrated drastically reduced antimitotic activity ($IC_{50}$ 20000 nM). This demonstrates that reduction of the $\Delta^{2',3'}$ double bond is responsible for loss of antimitotic activity.

Example 4

The synthesis of 9 started from eleutherobin, through first forming the 3",4"-acetonide 11, which was subsequently deacetylated to the 2" alcohol and converted directly to the 2" TBS ether 12. Hydrogenation of 12, using catalytic Pd on BaSO4, gave the 5,6,11β,12,2',3'-hexahydro derivative wide supra (Table 3). Hydrolysis of the crude hydrogenation product cleanly removed the C-8 ester side chain, which was replaced with a urocanic ester residue 4c to afford 14. Deprotection of the tribromosalicylanilide (TBS) protecting group, followed by acetylation of the formed 2" alcohol provided 15, which was subsequently deprotected under mildly acidic conditions to give 5,6,11β,12-tetrahydro eleutherobin (9). Similarly, 2'3'-dihdro-eleutherobin (10) was prepared from the 2" TBS ether 12, by hydrolysis of the urocanic ester residue (NaOH, MeOH) to provide a secondary alcohol at C-8, which was directly coupled with 2,3-dihydro-urocanic acid (17) using 1,3dichlorohexylcarbodiimide (DCC) and 4-dimethylaminopyridine (DMAP) in warm (50° C.) dimethyl formanide (DMF) to afford 15. A deprotection/acetylation sequence similar to that employed in the synthesis of the tetrahydro derivative 9, provided 10 in good yield. Compound 9 exhibited antimitotic activity ($IC_{50}$ 200 nM) comparable to eleutherobin while compound 10 demonstrated drastically reduced antimitotic activity ($IC_{50}$ 20000 nM). This demonstrates that reduction of the $\Delta^{2',3'}$ double bond is responsible for loss of antimitotic activity.

TABLE 3
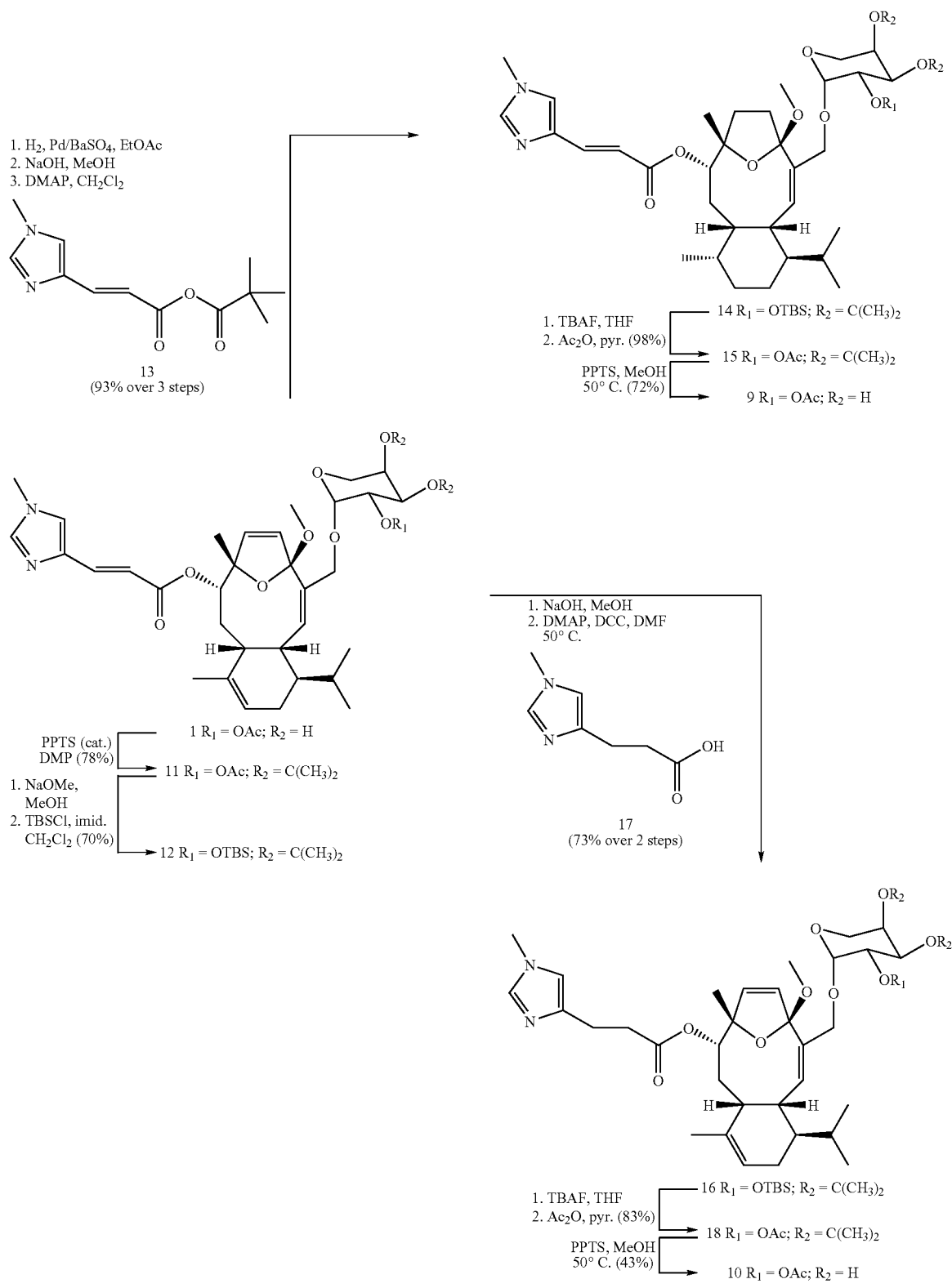
Selective Modifications at C-17
Labelling of substituents (e.g. $R^3$–$R^6$) in the structural formulae set out in Tables 4–8 below is not the same as the labelling of the corresponding substituents (e.g. $R_1$–$R_4$) in the definition of compounds of this invention as set out above. Labelling used in the following Tables is for convenience in following the synthesis schemes described in Examples 5–9. In any case, substituents of compounds of this invention may be recognized by their position in a structural formula and by reference to the description above.

Example 5

As demonstrated in Example 2, the C-17 methyl group of eleutherobin is readily oxidized with $SeO_2$ in refluxing ethanol to provide an allylic alcohol at C-17. This reaction is again shown in Table 4 with compound (X) representing eleutherobin or an analog thereof to produce compound (XV). Using compound (XV) as an intermediate, a number of reactions may be undertaken to further modify the functionality at C-17 (Table 4). These reactions are preferably undertaken when the C-3" and C-4" OH's are protected as an acetonide or in some cases as ester. Examples of procedures for protecting and deprotecting the sugar OH's are given below. The allylic alcohol XV can be converted to esters XXIV by reaction with anhydrides. As outlined in Table 4, this alcohol may also be converted to a halide ($PPh_3$, imid, $X_2$), to provide an allylic halide XVI. This allylic halide may be displaced by a number of nucleophiles under standard conditions to provide compounds of general structure XVII. In addition, the allylic alcohol may be oxidized to an aldehyde (TPAP, NMO, $CH_2Cl_2$) such as XVIII, and further oxidized (t-butanol, 2-methyl-2-butene, $NaH_2PO_4$, $NaClO_2$, $H_2O$) to the corresponding carboxylic acid (XIX). Examples of simple modifications of both the aldehyde XVIII and the acid XIX are set out in Table 4. As the aldehyde functionality in XVIII represents the most electrophilic centre in the molecule, it may be coupled with a variety of Wittig type nucleophiles under standard conditions to provide alkenes of general structure XX. Alternatively, the aldehyde functionality may be coupled with a number of standard nucleophiles to provide a secondary alcohol of general structure XXI. The carboxylic acid functionality in XIX may also be selectively reacted with various alcohols (to provide esters XXII) or amines (to provide amides XXIII). Modifications of the C-17 methyl moiety (and the subsequent modifications to the aldehyde XVIII and the acid XIX) that are described above may also be applied to compounds in which substitutions and modifications at C-4, and C-2", C-3" and C-4" of the sugar moiety have also been undertaken.

TABLE 4

Selective Modifications at C-17

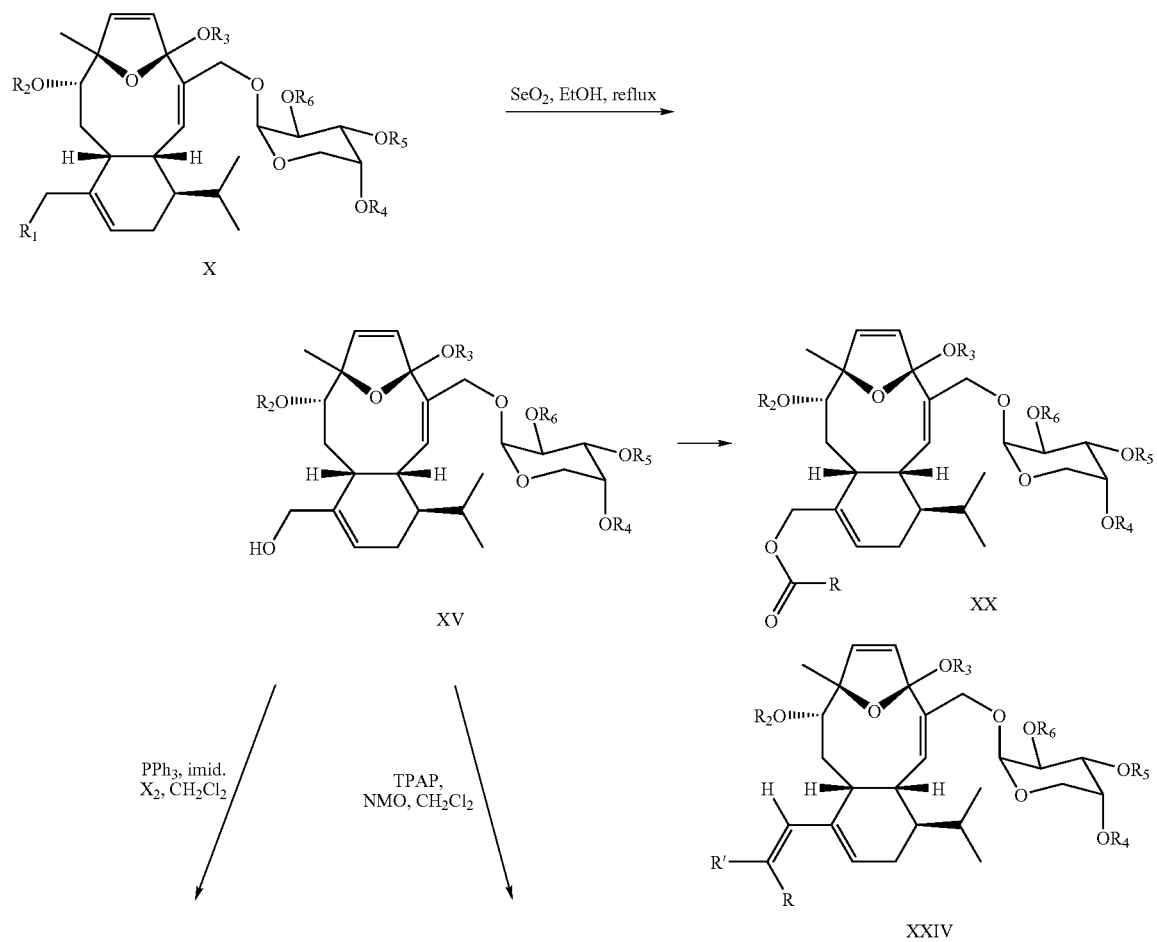

TABLE 4-continued

Selective Modifications at C-17

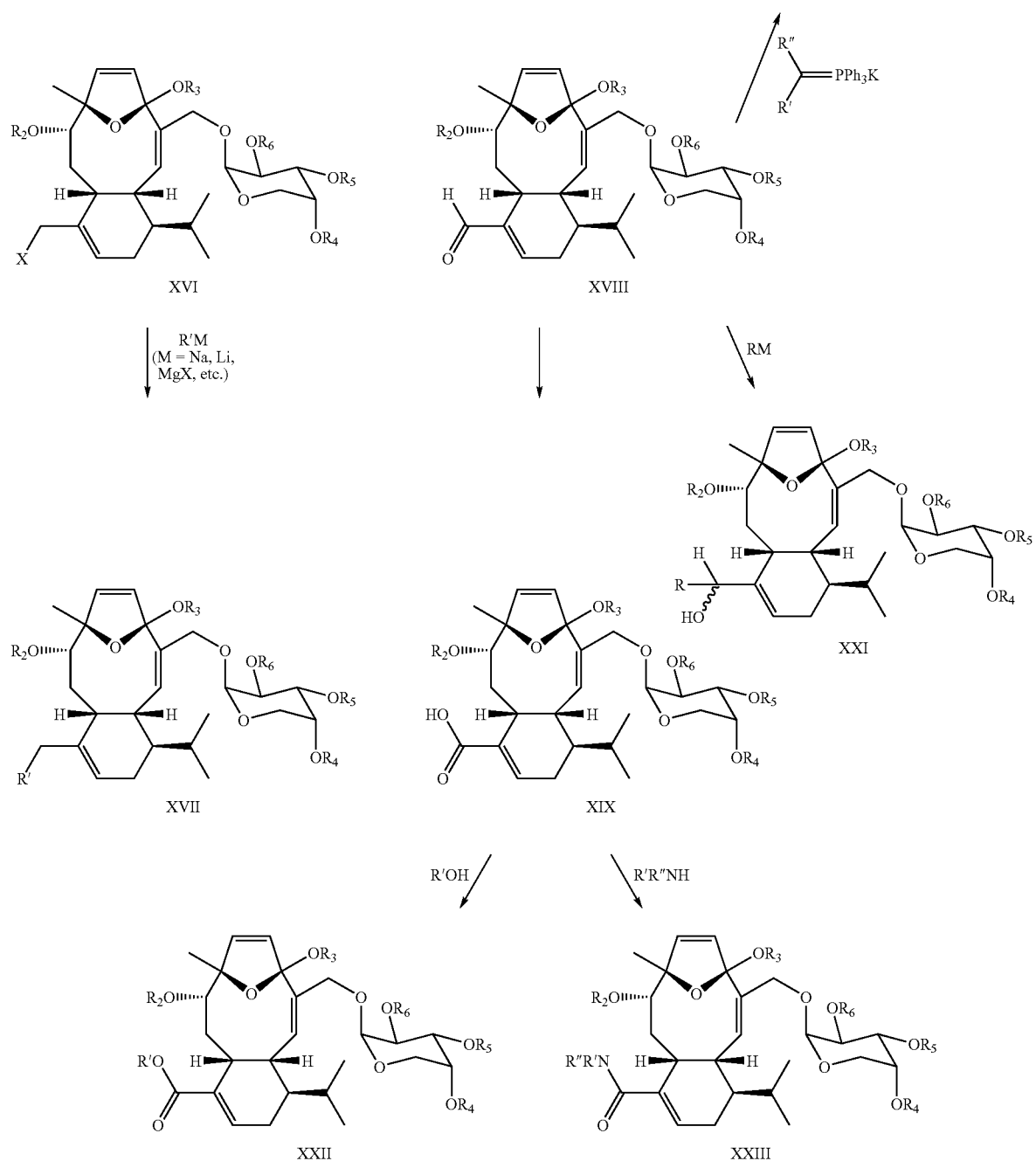

Example 6

Some transformations described in Example 5 rely primarily on the ability to efficaciously transform the substituents on the sugar appendage at C-15 of eleutherobin. Concurrent protection of the C-3" and C-4" hydroxyl groups of eleutherobin (I) to provide eleutherobin acetonide (II) are possible as is shown in Table 5. Eleutherobin acetonide (II) may be an intermediate for use in further modifications. A sequence of reactions which allows access to a uniquely substituted sugar is described in Table 5. The acetate appendage at C-1" in eleutherobin acetonide may be selectively hydrolized to provide III, which can be coupled with a variety of protecting agents (such as tert-butyldimethylsilylchloride) to provide a structure such as IV. With the sugar suitably protected, the core (C-1 to C-20) of eleutherobin may be further functionalized or modified. In particular, substitutions of various polar, nonpolar and bulky alkyl groups for the methyl ketal at C-4 ($R_3$), and functionalization of the methyl group ($R_1$) and replacement of the N-methyl urocanic ester residue (R$_2$) at C-8 with a variety of α,β-unsaturated esters provides expedient access to new series of eluethesides, As outlined in Table 5, with various substitution patterns at the C-4 ketal, the C-8 hydroxyl and the methyl at C-17, the protection group at C-2" may be removed under standard conditions to provide a free hydroxyl which can then be subsequently acetylated to afford compounds of general formula VI. The remaining acetonide protecting group is cleanly removed under mildly acidic conditions to provide a compound in which the sugar moiety is identical to that found in eleutherobin with the core (C-1 to C-20) capable of being modified as described below.

TABLE 5

Protection/deprotection of Eleutherobin (I)

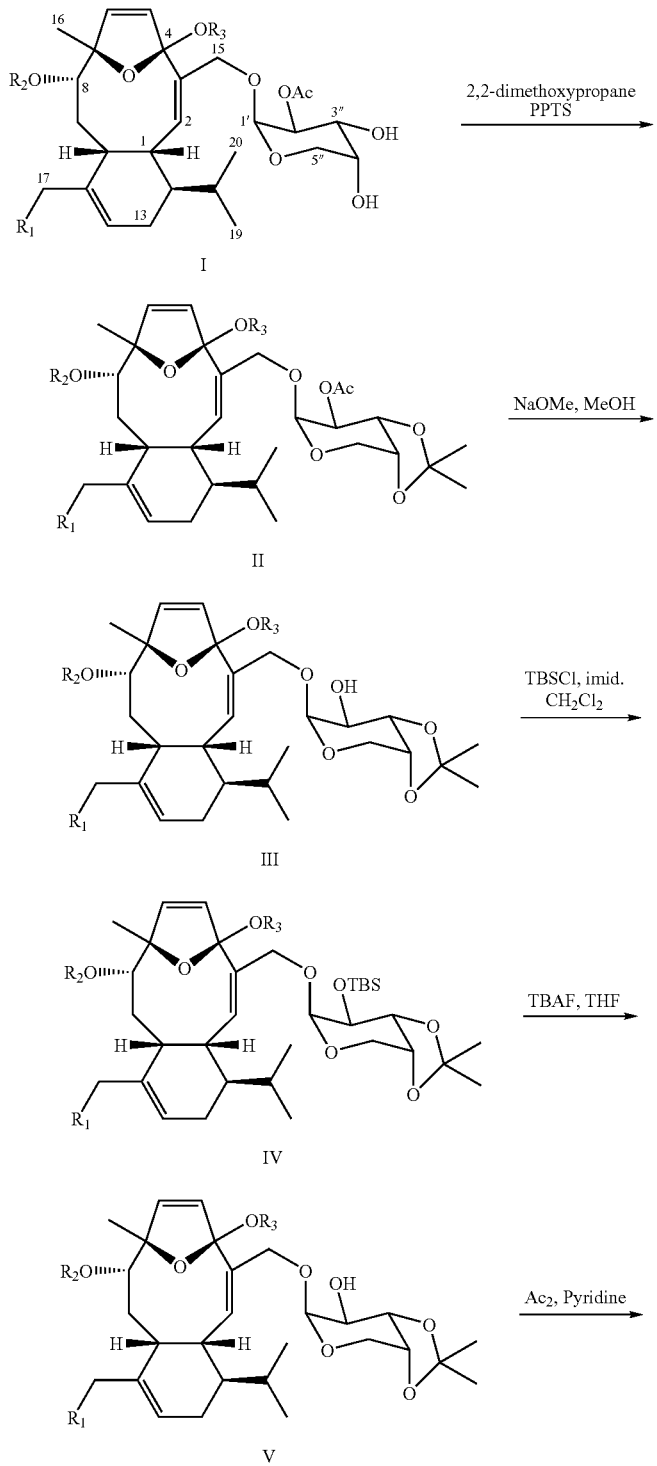

TABLE 5-continued

Protection/deprotection of Eleutherobin (I)

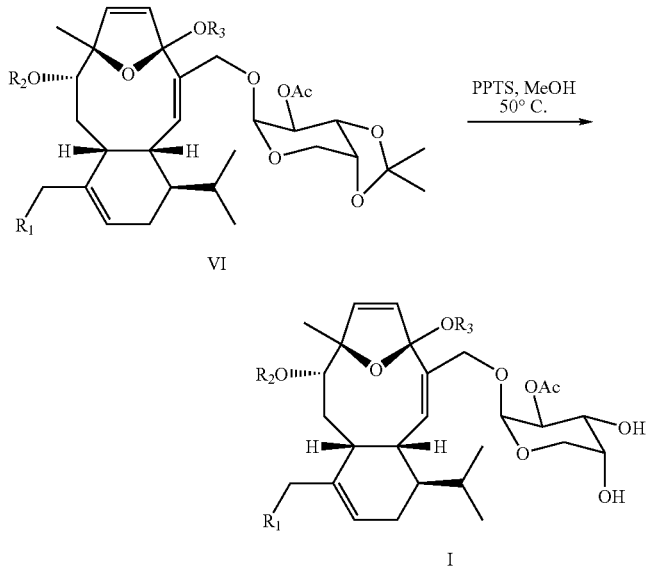

Example 7

As outlined in Example 6, the sugar appendage may be selectively protected and further functionalized. An intermediate such as IV may be deprotected through an alternative sequence (Table 6) whereby access to a sugar moiety selectively substituted at C-2", C-3" and C-4" is gained. Initial deprotection of the C-3" and C-4" acetonide provides access to a compound of general structure VI. Taking advantage of the inherent differences in reactivity between an axial (C-4") hydroxyl and an equatorial (C-3") hydroxyl, the substituents at both C-3" and C-4" may be selectively introduced to provide a compound of general structure VIII. The protecting group at C-2" can subsequently be removed and replaced by a variety of substituents to provide X (Table 6) in which the sugar moiety is now uniquely functionalized at C-2", C-3" and C-4". These modifications of the sugar moiety may also be applied to compounds in which substitutions and modifications at C-4, C-8 and C-17, such as are described in Example 8, are undertaken.

TABLE 6

Selective Substitution on Sugar

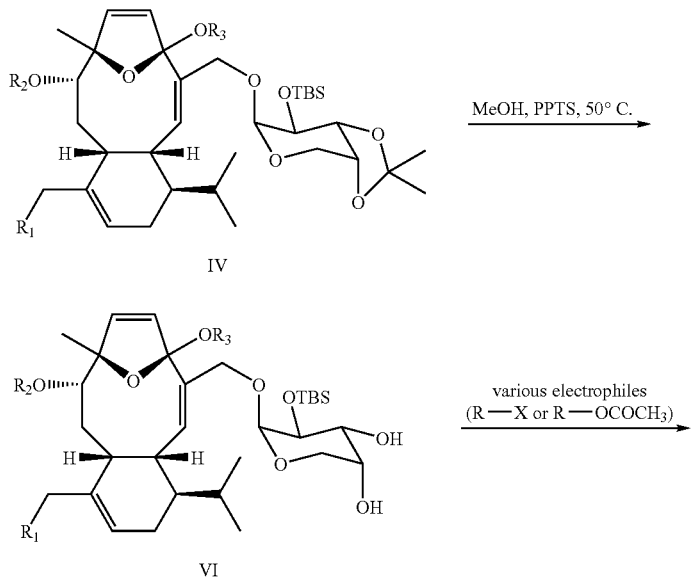

TABLE 6-continued

Selective Substitution on Sugar

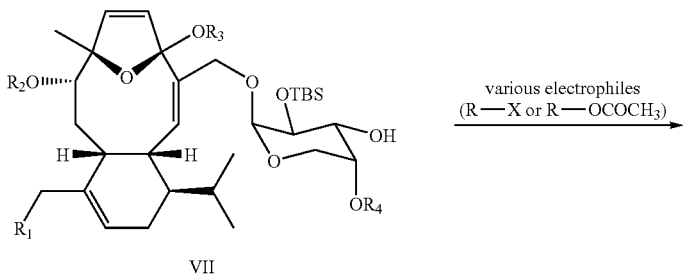

VII various electrophiles
(R—X or R—OCOCH₃) →

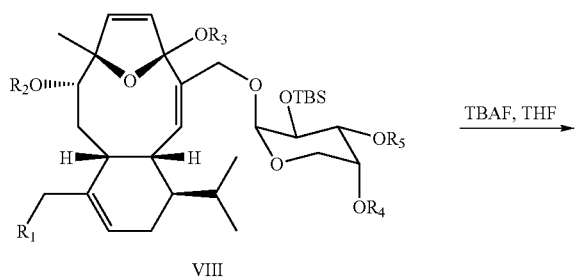

VIII

TBAF, THF →

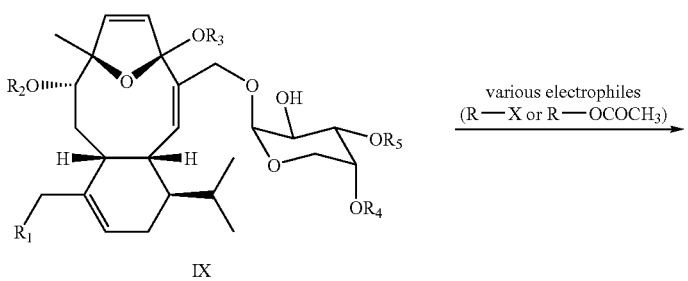

IX various electrophiles
(R—X or R—OCOCH₃) →

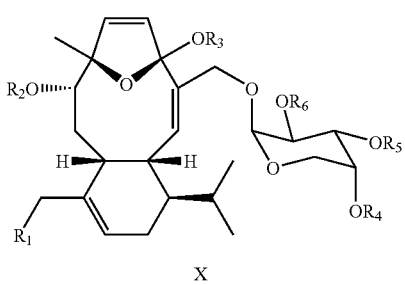

X

Example 8

The methyl ketal functionality present in eleutherobin at C-4 may be converted to a variety of bulky, polar or nonpolar ketals through a transketalization reaction catalyzed by PPTS. As depicted in Table 7, this transformation lends access to a series of new eleuthesides and can be undertaken in situations where C-17, C-8 and the sugar moiety are variously substituted.

TABLE 7

Selective Transketalization

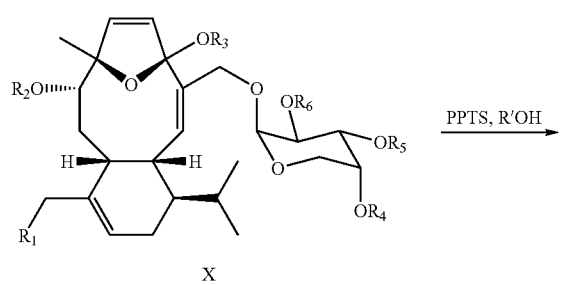

X $R_1 = H$, $R_2 = $ N-methylurocanate
$R_3 = $ Me, $R_4$, $R_5 = H$, $R_6 = $ Ac
(eleutherobin)

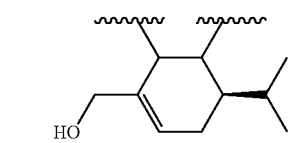

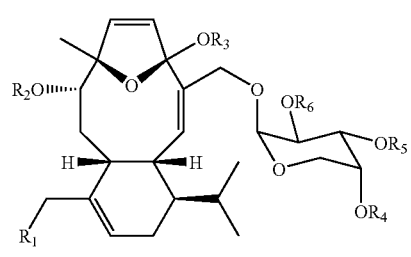

XI $R_1 = H$, $R_2 = $ N-methylurocanate
$R_3 = R'$, $R_4$, $R_5 = H$, $R_6 = $ Ac

Example 9

Table 8 sets out various examples of compounds of formula I of this invention which are made using standard techniques from an alcohol or carboxylic acid moiety at C-11. Included are examples where moiety X of compounds of formula I includes a moiety (Q) intended to enhance in vivo delivery (e.g. a lipid such as is found in a lipid-based delivery vehicle such as a liposome) or a biologically active moiety (such as an antibody or hormone intended to enhance targeting of the compound to a cell type, cell receptor, etc.). Moiety Q may include a linker used to join a moiety such as a lipid, antibody, hormone, etc. to C-11. Such linkers may be designed to be cleaved in certain environments or under particular conditions to enhance release of the antimitotic moiety from Q at or in a target cell.

Compounds shown in Table 8 as coming from compounds 5 or 6 of Table 2 are examples of compounds which may be readily made from compounds of formula II of this invention.

TABLE 8

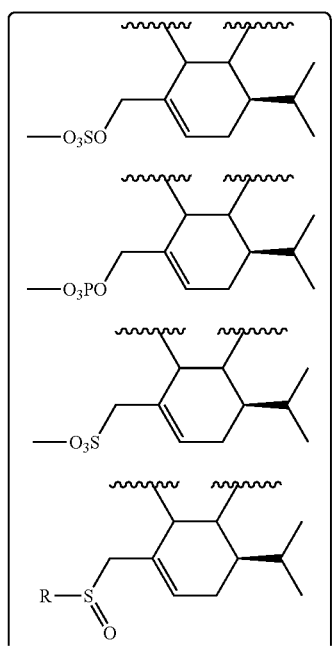

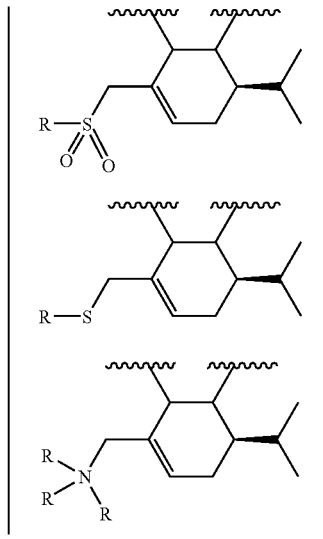

TABLE 8-continued
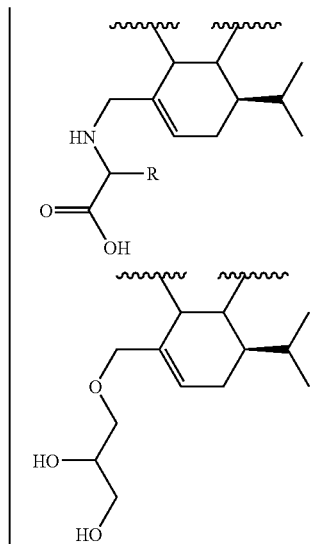
From XVI, TABLE 4
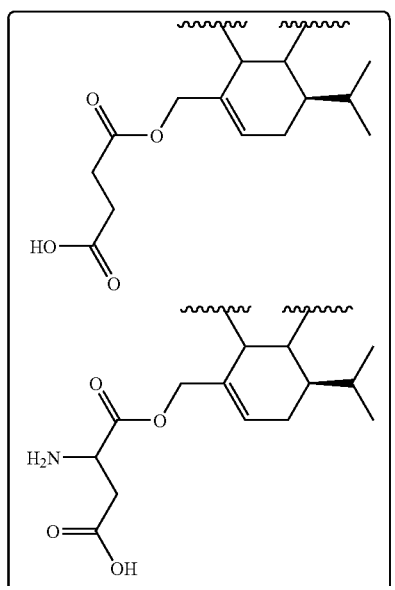
TABLE 8-continued
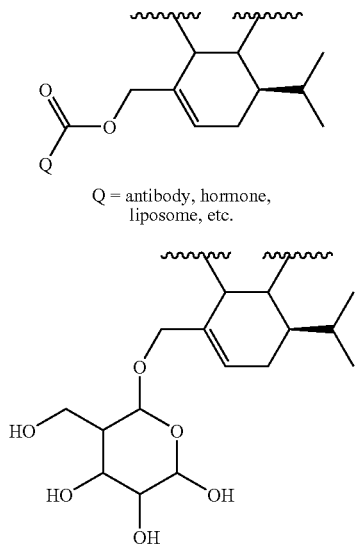
Q = antibody, hormone, liposome, etc.
From XV, TABLE 4
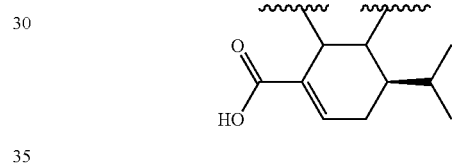
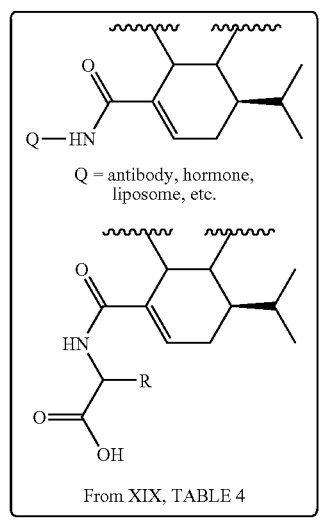
Q = antibody, hormone, liposome, etc.
From XIX, TABLE 4
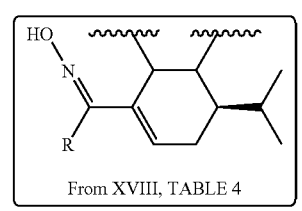
From XVIII, TABLE 4

TABLE 8-continued

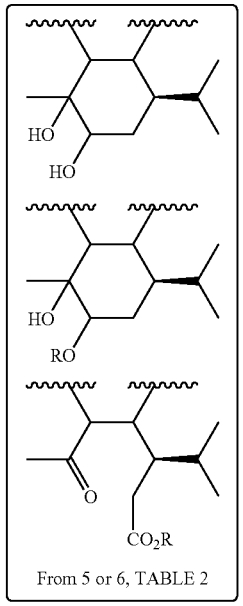

From 5 or 6, TABLE 2

All publications, patents and patent applications referred to herein are hereby incorporated by reference. While this invention has been described according to particular embodiments and by reference to certain examples, it will be apparent to those of skill in the art that variations and modifications of the invention as described herein.

We claim:

1. A compound or pharmaceutically acceptable salt thereof, wherein the compound is of formula I or II:

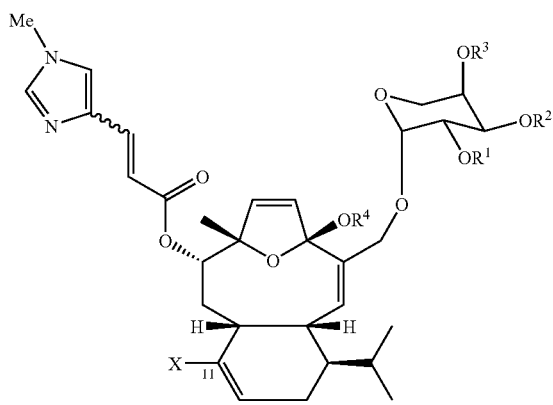

I

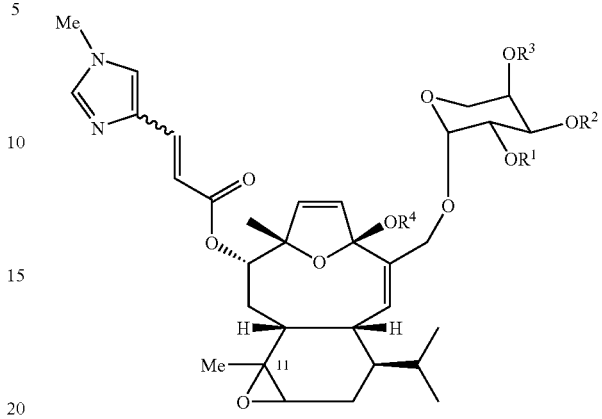

II wherein, Me is methyl; $R^1$, $R^2$ and $R^3$ are independently selected from the group consisting of: H and $C_1$–$C_6$ acyl; $R^4$ is selected from the group consisting of: H,Me and a substituted or unsubstituted straight-chain, branched, or cyclic $C_1$–$C_{10}$ alkyl; and, X is selected from the group consisting of: —$CH_2OR$, —COR, —COY, —C(OR)R, —CRCR$_2$, and, —CH$_2$W; R is selected from the group consisting of: H; a linear, branched, or cyclic, saturated or unsaturated alkyl group containing one to ten carbons optionally substituted with Z; an aromatic group optionally substituted with Z; and, arylalkyl (ArR*) in which an alkyl group (R*) is a linear, branched, or cyclic, and saturated or unsaturated containing one to ten carbons a optionally substituted with Z and an aryl group (Ar) optionally substituted with Z; Z is selected from the group consisting of: —OH, —OR, —O$_2$CR, —SH, —SR, —SOCR, —NH$_2$, —NHR, —NHR$_2$, —NHCOR, —NRCOR, —I, —Br, —Cl, —F, —CN, —CO$_2$H, —CO$_2$R, —CHO, —COR, —CONH$_2$, —CONHR, —CONR$_2$, —COSH, —COSR, —NO$_2$, —SO$_3$H, —SOR, and —SO$_2$R; Y is selected from the group consisting of: —OH, —NH$_2$, —NHR, —NR$_2$, —SH, —SR and —OR; W is selected from the group consisting of: R, F, Cl, Br, I, 13 OSO$_3$R, —SO$_3$R, —OPO$_3$R$_2$, —PO$_3$R$_2$, —SR, —SOR, —SO$_2$R, —NR$_2$, —NOR, and —NR$_3^+$; with each R being the same or different, and wherein for R* and for R when comprising an alkyl, —CH$_2$— may be replaced by —O$_2$S or NR and CH may be replaced by N; and wherein W=R, R cannot be methyl or ethyl.

2. A compound of claim 1, wherein $R^1$ and $R^2$ are H and $R^3$ is acyl.

3. A compound of claim 1, wherein one of $R^1$ and $R^2$ is H, and the other of $R^1$ and $R^2$ is acyl and, $R^3$ is H.

4. A compound of claim 1, wherein one or more of $R^1$–$R^4$ is acetyl.

5. A compound of claim 2 or 3, wherein acyl is acetyl.

6. A compound of claim 1, wherein one or more of $R^1$–$R^4$ is a $C_2$–$C_5$ straight-chain or branched alkyl.

7. A compound of claim 1, wherein $R^4$ is selected from the group consisting of: H, ethyl, propyl, butyl and pentyl.

8. A compound of claim 1, wherein $R^1$ and $R^3$ are H; $R^2$ is acyl; and, $R^4$ is methyl.

9. A compound of claim 8, wherein $R^2$ is acetyl.

10. A compound of claim 1, wherein R is: H; or, a linear, branched or cyclic, saturated or unsaturated alkyl group; and, Y is selected from the group consisting of: OH, $NH_2$, NHR, $NHR_2$ and OR.

11. A compound of claim 1, wherein R is H or a $C_1$–$C_6$ branched or straight chain alkyl.

12. A compound of claim 1, wherein X is selected from the group consisting of: —COH; —COOH; —$CNH_2$; —CNHR; —$CNR_2$; and, —COR.

13. A compound of claim 12, wherein R is a $C_1$–$C_6$ branched or straight chain alkyl.

14. A compound of claim 1, wherein X is —$CH_2OH$.

15. A compound of claim 1, wherein the compound is of formula II.

16. A compound of claim 15, wherein the epoxide at C-11 is in a β configuration.

17. A pharmaceutical preparation comprising a compound or pharmaceutically acceptable salt of claim 1 and a pharmaceutically acceptable carrier or diluent.

* * * * *